United States Patent [19]

Horgan et al.

[11] 4,191,828
[45] Mar. 4, 1980

[54] PROCESS FOR PREPARING 2-(2,2-DICYCLOHEXYLETHYL)PIPERIDINE

[75] Inventors: Stephen W. Horgan; Frank P. Palopoli, both of Montgomery, Ohio; David L. Wenstrup, Edgewood, Ky.

[73] Assignee: Richardson-Merrell Inc., Wilton, Conn.

[21] Appl. No.: 677,036

[22] Filed: Apr. 14, 1976

[51] Int. Cl.$^2$ .............................................. C07D 24/02
[52] U.S. Cl. ................................... 546/185; 546/344; 546/350
[58] Field of Search ..................... 260/293.52; 546/185

[56] References Cited

U.S. PATENT DOCUMENTS

| | | | |
|---|---|---|---|
| 2,675,390 | 4/1954 | Rosenblatt | 260/293.52 |
| 3,252,982 | 5/1966 | Mizzoni et al. | 546/229 |

FOREIGN PATENT DOCUMENTS

| | | | |
|---|---|---|---|
| 904117 | 8/1962 | United Kingdom | 260/293.52 |
| 1025578 | 4/1966 | United Kingdom | 546/185 |

OTHER PUBLICATIONS

Sury, E., et al., *Helv. Chim. Acta*, ", 2133–2145 (1954).
Freifelder, et al., J. Org. Chem. 27:284–286 (1962) [cited as Chem. Abs. 57:777 (1962)].

*Primary Examiner*—Alan L. Rotman
*Assistant Examiner*—Richard A. Schwartz
*Attorney, Agent, or Firm*—William J. Stein; Eugene O. Retter; George W. Rauchfuss, Jr.

[57] ABSTRACT

2-(2,2-Dicyclohexylethyl)piperidine is prepared via the catalytic hydrogenation of 2-(2,2-diphenylethenyl)pyridine in a single step. High yields are obtained using a rhodium supported catalyst.

1 Claim, No Drawings

PROCESS FOR PREPARING 2-(2,2-DICYCLOHEXYLETHYL)PIPERIDINE

BACKGROUND OF THE INVENTION

The compound 2-(2,2-dicyclohexylethyl)piperidine, known by its generic name perhexiline, is a well-established chemical entity. In the form of its maleate salt it is used for the prevention of angina pectoris in patients with coronary artery disease. Perhexiline maleate can be represented by the following chemical structural formula:

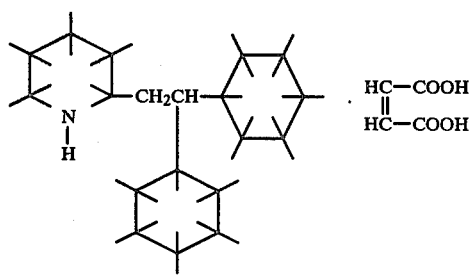
(Ia)

In the past, perhexiline (I) has been prepared by reacting α-picoline (II) with phenyl-lithium to form α-picolyl-lithium. The α-picolyl-lithium is not isolated but condensed with dicyclohexyl ketone (III) to form α,α-dicyclohexyl-2-pyridineethanol (IV). Dehydration of the pyridineethanol using a conventional dehydrating agent, such as phosphoric acid (85%), alcoholic hydrogen chloride or hydrogen bromide results in the preparation of 2-(2,2-dicyclohexylethenyl)pyridine (V), as shown in U.S. Pat. No. 3,038,905. Hydrogenation of the pyridine ring and the double bond to form perhexiline is accomplished using low pressure hydrogen (4 atmospheres) in the presence of a platinum oxide catalyst, as disclosed in British Patent No. 1,025,578. This reaction sequence can be depicted as follows:

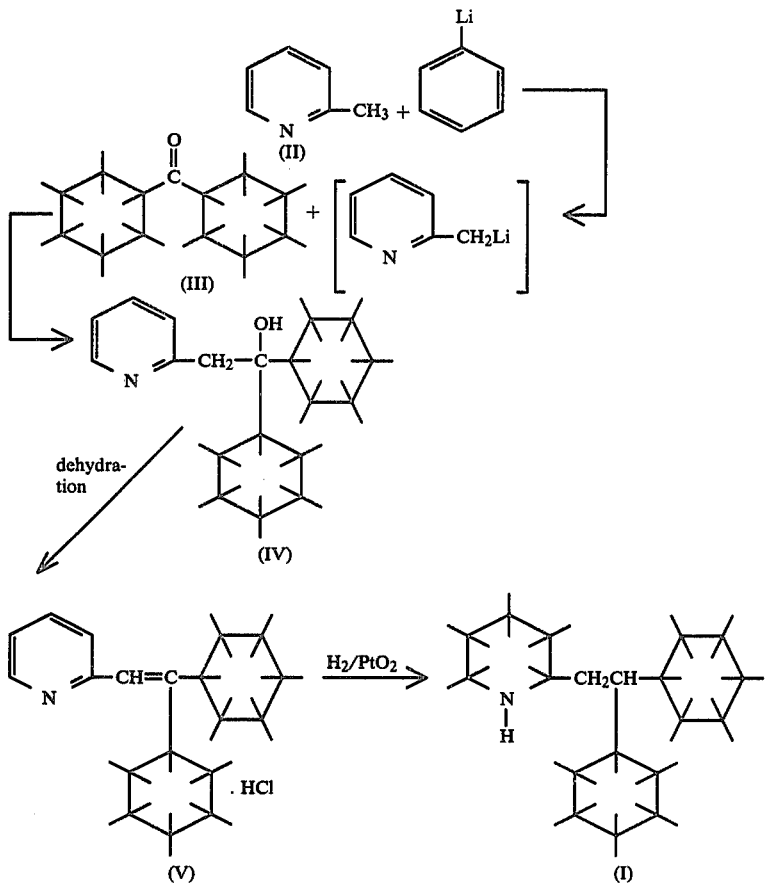

The fully aromatic intermediates have also been previously prepared. Thus, a refluxing mixture of α-picoline (II), benzophenone (VI) and lithium amide yields α,α-diphenyl-2-pyridineethanol (VII) in accordance with the procedure set forth by Tilford et al., J. Am. Chem. Soc. 76, 2431, 2434 (1954). Dehydration of the pyridineethanol with dilute hydrochloric acid or 48 percent HBr results in the preparation of 2-(2,2-diphenylethenyl)pyridine (VIII). This reaction sequence can be indicated as follows:

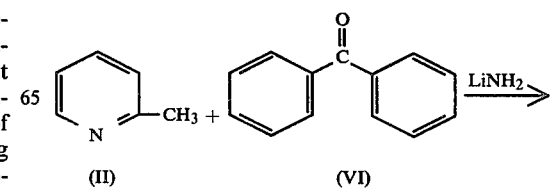

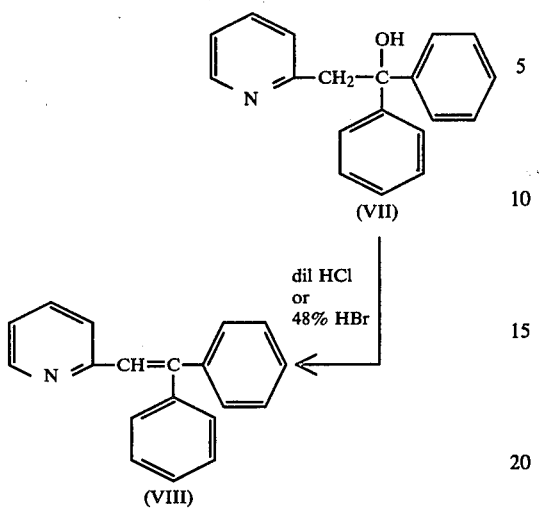

(VII)

dil HCl or 48% HBr (VIII)

However, previous attempts to reduce the double bond, piperidine ring and the two phenyl rings of 2-(2,2-diphenylethenyl)pyridine (VIII) in a single step to obtain perhexiline (I) directly have heretofore been unreported.

SUMMARY OF THE INVENTION

In accordance with this invention, perhexiline (I) is directly prepared in a one-step process by the reduction of 2-(2,2-diphenylethenyl)pyridine (VIII). More particularly, the process of the present invention comprises reducing a mixture of either 2-(2,2-diphenylethenyl)pyridine or a salt thereof in a solvent selected from the group consisting of acetic acid or a lower alkanol having from 1 to 4 carbon atoms using hydrogen at a pressure of from 14 to 140 atmospheres and at a temperature of from 90° to 200° C. in the presence of a rhodium supported catalyst. Not only does this process result in the reduction of the double bond and the pyridine ring as expected, but results surprisingly in a simultaneous reduction of both phenyl rings as well. However, even more surprisingly, the amount of rhodium catalyst which must be present in order for the reduction to proceed is critical with respect to the 2-(2,2-diphenylethenyl) pyridine present. This reaction can be schematically illustrated as follows:

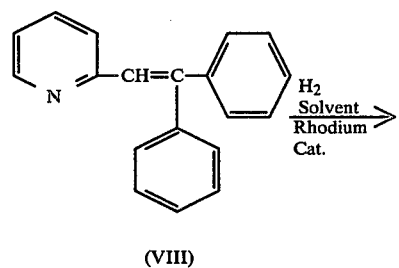

(VIII)

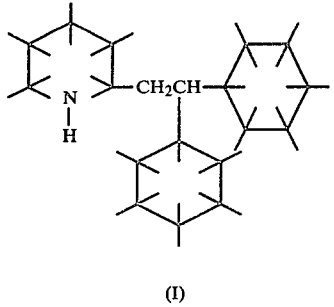

(I)

DETAILED DESCRIPTION OF THE INVENTION

Previously, the reduction of compounds analogous to 2-(2,2-diphenylethenyl)pyridine resulted only in a reduction of the heterocyclic portion of the molecule. Thus, Sury et al., *Helv. Chim. Acta* 2133, 2142 (1954) teach the selective reduction of 2-(2,2-diphenylmethyl)-pyridine and related aromatic pyridines to the corresponding piperidines using either a platinum oxide catalyst or a Raney nickel catalyst. U.S. Pat. No. 3,252,982 describes the catalytic hydrogenation of 3-benzhydryl-pyridines to the corresponding 3-benzhydrylpiperidines. However, the simultaneous reduction of the double bond, pyridine ring and both phenyl rings has hithertofore been unreported.

Applicants have discovered a process whereby the compound 2-(2,2-diphenylethenyl)pyridine (VIII) or a salt thereof can be completely reduced in a single step. The process of this invention provides a safe and economical method for the preparation of perhexiline, and is readily adapted to large scale batch or continuous production. Moreover, when prepared in accordance with the teachings of the present invention, perhexiline is obtained in high purity in yields as high as 90 to 99%.

The starting material 2-(2,2-diphenylethenyl)pyridine (VIII) is readily prepared by the condensation of α-picoline and benzophenone in the presence of lithium amide to form α,α-diphenyl-2-pyridineethanol as illustrated in Example 1. Dehydration by means of phosphoric acid (85%), hydrobromic acid (48%) or hydrochloric acid to prepare the 2-(2,2-diphenylethenyl)pyridine starting material is illustrated in Example 2. Alternatively, the pyridineethanol compound may be dehydrated in situ, as illustrated in Example 3, this being a preferred route in the large scale production of perhexiline.

The reduction of 2-(2,2-diphenylethenyl)pyridine, or a salt thereof, to obtain perhexiline is conducted in a suitable reduction solvent in accordance with the process of this invention. Suitable salts of 2-(2,2-diphenylethenyl) pyridine which can be employed include salts of inorganic acids, as for example, hydrochloric, hydrobromic or phosphoric acid, and salts formed with organic acids, such as acetic, propionic, malonic and succinic acids. Suitable reduction solvents include acetic acid or a lower alkanol having from 1 to 4 carbon atoms including methanol, ethanol, propanol, isopropanol, butanol, isobutanol and t-butanol. Preferably, the free base is added to acetic acid as the reduction solvent, resulting in the amino nitrogen of the pyridine ring being in a protonated form. Alternatively, the 2-(2,2-diphenylethenyl)pyridine is reduced in a lower alkanol in the form of a protonated salt, ethanol being the alkanol of choice.

The catalyst employed in the process of this invention is critical and contains elemental rhodium supported on any of the carriers conventionally employed for this purpose. Examples of such carriers include carbon, alumina, kieselguhr, bentonite, asbestos, silica gel and zirconium oxide. The preferred carriers employed in the process of this invention are carbon and alumina. Inasmuch as many of the supported rhodium catalysts employed by the process of this invention are readily available from commercial sources, the actual preparation of a rhodium supported catalyst can be avoided if desired. Commercially available catalysts include various concentrations ranging from 5 to 30% of rhodium-on-carbon or rhodium-on-alumina, wherein the carbon or alumina can be in a finely divided amorphous, granular or pelletized state. Alternatively, the rhodium supported catalyst can be prepared by suspending the desired carrier in an aqueous solution of a soluble rhodium salt, such as rhodium chloride trihydrate. The mixture is treated with a base so as to deposit rhodium hydroxide on the support substrate. When shaken in an atmosphere of hydrogen, the rhodium salt is reduced to its elemental state supported on the carrier.

The amount of rhodium catalyst employed in accordance with the process of this invention is critical, being proportional to the amount of 2-(2,2-diphenylethenyl)-pyridine employed. The term "catalyst loading" refers to that percentage of rhodium present, expressed in parts by weight per 100 parts by weight of 2-(2,2-diphenylethenyl)pyridine. As can be seen from the data presented in Example 6, no product is obtained if the reduction is carried out with catalyst loadings of less than 0.1 percent. Furthermore, catalyst loadings of 0.15 to 0.20 percent result in only a partial reduction of 2-(2,2-diphenylethenyl)pyridine to perhexiline, whereas catalyst loadings of 0.25 to 0.75 percent result in 97.7 to 99.9 percent reduction to perhexiline. Thus, a catalyst loading of 0.15 percent clearly represents the minimum amount of catalyst that can successfully be employed, whereas the maximum amount of rhodium support catalyst that can be utilized is dictated only by the economics of the situation.

The catalyst loading is independent of the particular concentration of rhodium supported catalyst employed. Thus, for example, if a catalyst loading of 0.50 percent is employed, similar results are obtained whether one utilizes 10 parts by weight of a 5 percent rhodium on carbon catalyst per 100 parts by weight of 2-(2,2-diphenylethenyl)pyridine or 5 parts by weight of a 10 percent rhodium on carbon catalyst.

In commercial operation, the catalyst is recycled for reasons of economy. Inasmuch as the catalyst is subject to gradual poisoning and fouling, its efficiency becomes retarded with continued usage. Therefore, in catalyst recycling operations, catalyst loadings of 0.75 percent or higher are commonly employed.

The process of this invention requires relatively high hydrogen pressures in order for the reaction to be completed within a reasonable period of time. Hydrogen pressures can vary over a wide range of from about 14 to about 140 atmospheres. Preferably, however, the reaction is conducted at a hydrogen pressure of from about 20 to about 50 atmospheres. In general, the higher the hydrogen pressure, the faster the rate of reduction. Thus, at approximately a one molar concentration of 2-(2,2-diphenylethenyl)pyridine, a temperature of 115° C. and a hydrogen pressure of 40 atmospheres, the reduction is essentially complete in about 2.75 hours, whereas under hydrogen pressure of 24 atmospheres, the reduction requires approximately 4.25 hours for completion.

The progress of the reduction is readily followed by observing the amount of hydrogen taken up by the reaction mixture. Theoretically 10 moles of hydrogen per mole of 2-(2,2-diphenylethenyl)pyridine are required for complete reduction. On large scale production batches, the main pressure gauge of the hydrogen source can be used to monitor the progress of the reduction and reduction is continued until no further hydrogen uptake is observed.

The reduction is conducted at a temperature within the range of 90° to 200° C. The particular choice of temperature selected is a function of both the hydrogen pressure and the reduction period. Thus, the higher the hydrogen pressure, the lower the reaction temperature required for reduction within the above limits. Similarly, the higher the reaction temperature, the more rapid the rate of reduction. If the reduction is conducted much beyond 200° C., thermal degradation of the reaction mixture is noted. Preferably, the reduction is conducted within a temperature range of from 120° to 150° C.

In general, the process of this invention is conducted in a solvent as a batch-operated heterogeneous reduction. An aqueous slurry of the rhodium supported catalyst is added to an appropriate reactor or autoclave previously purged with nitrogen or some other inert gas. The 2-(2,2-diphenylethenyl)pyridine or a salt thereof is dissolved in acetic acid or one of the lower alkanols previously described and charged to the reactor and the system again purged with nitrogen or some other inert gas. Hydrogen gas is introduced into the system to the desired pressure and the reaction mixture stirred and heated to its operating temperature. Hydrogenation is continued for approximately 3 to 4 hours or until hydrogen uptake ceases. The reaction mixture is cooled and the catalyst removed by filtration. Perhexiline can be recovered from the filtrate in accordance with well-known procedures, as for example, extraction or via solvent removal techniques.

A preferred method for the recovery of perhexiline is as its maleate salt. This salt has the further advantage of being obtained from the reaction mixture in almost quantitative yields. Moreover, the maleate is the particular salt form in which perhexiline is therapeutically administered. Following reduction, the catalyst is removed, washed and the combined filtrates are evaporated in vacuo. When acetic acid is used as the reduction solvent, an oily residue of perhexiline acetate is obtained. The perhexiline residue is dissolved in a crystallizing solvent such as acetone, methyl ethyl ketone or one of the lower alkanols previously described. The preferred crystallizing solvents for the recovery of perhexiline maleate are acetone or isopropanol.

A solution of maleic acid is prepared using the same crystallizing solvent and warmed to about 40°–50° C. The maleic acid solution is rapidly added with efficient stirring to the perhexiline solution, whereupon the perhexiline maleate precipitates. The solution is cooled to a final temperature of 15°–20° C. The product is removed by filtration, washed with cold crystallizing solvent and is obtained in high yield of excellent purity having a m.p. of 186°–189° C. A final recrystallization from methanol yields pharmaceutical grade material having a m.p. of 189°–191° C. Recovery of perhexiline maleate via this acetone procedure is so efficient that it can be utilized as a means for quantitating the amount of perhexiline formed during reduction.

Another preferred embodiment of this invention employs the use of a fixed bed catalyst or a trickle bed reactor as a continuous process. In its physical form the reactant solution is fed into a fixed bed or trickle-bed column packed with pelleted or granular catalyst and permitted to trickle through the catalyst bed. Hydrogen gas is passed through the catalyst bed either concurrently or counter-currently to the liquid flow. The reaction takes place between the dissolved gas and liquid reactant at the catalyst surface. The product, which is continuously formed, is collected and removed from the bottom of the catalyst bed. In addition to providing for continuous operation, such a system has the advantage of eliminating the necessity of separating the catalyst from the reaction product at the completion of a batch reaction. Multiple feed passes and recyclizations can be easily installed to increase the efficiency of the reduction. Simplicity and reduced production costs make this continuous process highly desirable for large-scale commercial operation.

The following specific Examples more clearly illustrate the process of making and using this invention and set forth the best mode contemplated by the inventors for carrying out their invention. However, these illustrations are not to be construed as limiting the scope of the invention claimed.

EXAMPLE 1

$\alpha,\alpha$-Diphenyl-2-Pyridineethanol

Benzophenone, 32.4 kg (177.8 mole), $\alpha$-picoline, 33.1 kg (355.5 moles), and lithium amide, 4.54 kg (197.4 moles) are charged into a 30 gallon reactor arranged for reflux operation. The mixture is stirred, rapidly heated to 125° C. and maintained at this temperature. The rate of ammonia evolution will gradually increase and after about 3 to 4 hours of reaction time only occasional heating is required to maintain the desired temperature and a rapid evolution of ammonia. After about 5 hours, a vigorous surge of ammonia evolution is noted. Following the ammonia surge, external heating is continued and the reaction maintained at 125° C. for an additional 6 to 8 hours. The reaction mixture is cooled to 70°–80° C. and rapidly added to approximately 230 liters of water at 25° C. Stirring is continued for approximately 30 minutes and the solid removed by filtration. The filter cake is thoroughly washed with water and dried at 60°–70° C. yielding 42–6 kg of $\alpha,\alpha$-diphenyl-2-pyridineethanol having a m.p. of 147°–51° C.

EXAMPLE 2

2-(2,2-Diphenylethenyl)Pyridine

The compound $\alpha,\alpha$-diphenyl-2-pyridineethanol, 46.0 kg (167.1 mole) is added to a mixture of 44 liters of 37% hydrochloric acid and 44 liters of water. The reaction mixture is heated to its reflux temperature and maintained for one hour. Approximately 100 liters of water are added and the temperature of the reaction mixture adjusted to 25° C. On cooling, the hydrochloride salt separates as an oil. A cold solution of 19.4 kg of sodium hydroxide dissolved in 20 liters of water is added at such a rate as to maintain the temperature of the reaction mixture below 30° C. The 2-(2,2-diphenylethenyl)-pyridine base first separates as an oil which solidifies upon continued stirring and cooling. Stirring at 25°–30° C. is continued for approximately one hour to insure complete solidification of the product. The crude 2-(2,2-diphenylethenyl)pyridine is removed by filtration and washed with water until the final washing is essentially neutral. Approximately 43.0 kg of crude product is obtained having a melting point of 113°–7° C. Recrystallization of the crude material from isopropyl alcohol results in approximately 36.5 kg of 2-(2,2-diphenylethenyl)pyridine having an m.p. of 117°–9° C.

EXAMPLE 3

2-(2,2-Diphenylethenyl)Pyridine Prepared in situ

Benzophenone, 32.4 kg (177.8 moles), $\alpha$-picoline, 33.1 kg (355.5 moles), and lithium amide, 4.54 kg (197.4 moles) are placed in the reactor equipped for refluxing operation. The mixture is stirred and rapidly heated to its reflux temperature (125°–30° C.). The reaction mixture is maintained at its reflux temperature for approximately 3 to 4 hours. Occasional external heating is applied to maintain a rapid evolution of ammonia. After about 5 hours from the start of the reaction, a vigorous surge of ammonia evolution occurs. Following the ammonia surge, external heating is continued and the reaction maintained at 125° C. for a total period of about 12 hours. The reaction mixture is cooled to 100° C. and slowly added to a solution of 67 liters of 37% hydrochloric acid and 27 liters of water. The reaction mixture is heated to its reflux temperature and maintained at that temperature for a period of one hour. Approximately 60 liters of water are added and the temperature of the reaction mixture adjusted to about 25° C. During the cooling period, the hydrochloride salt of 2-(2,2-diphenylethenyl)pyridine separates as an oil. To the stirred reaction mixture is added a cold (5° C.) solution of 35.4 kg of sodium hydroxide (885 moles) contained in 42 liters of water at such a rate as to maintain the temperature of the reaction mixture below 30° C. The 2-(2,2-diphenylethenyl)pyridine base first separates as an oil, which upon continued stirring and cooling solidifies. Stirring is continued for approximately one hour at 25°–30° C. to ensure complete solidification of the product. The crude 2-(2,2-diphenylethenyl)pyridine is removed by filtration and washed well with water to yield 40.8 kg of material having an m.p. 103°–13° C. The crude product is dissolved in isopropyl alcohol, filtered, concentrated to remove about 20% of the isopropyl alcohol, and gradually cooled to 5° C. The desired 2-(2,2,-diphenylethenyl)pyridine is removed by filtration, washed with cold isopropyl alcohol to yield 34.1 kg of product having an m.p. of 117°–9° C.

EXAMPLE 4

2-(2,2-Dicyclohexylethyl)Piperidine Maleate

To a nitrogen-purged ten gallon autoclave is added a slurry of 400 g. of a 5 percent rhodium-on-carbon catalyst (Engelhard Industries) followed by a warm (50° C.) solution of glacial acetic acid and 4.0 kg (15.5 moles) of 2-(2,2-diphenylethenyl)pyridine. The charging system is rinsed using an additional 3.5 liters of glacial acetic acid. The system is purged with nitrogen and then hydrogen gas is introduced to a pressure of 40 atmospheres. The reaction mixture is stirred and heated to a temperature of about 115° C. Hydrogenation is continued at this temperature until no further hydrogen is taken up by the reaction mixture, usually a period of three to four hours. The reaction mixture is cooled to 30°-40° C. and the catalyst removed by filtration. The autoclave is rinsed several times with acetic acid which is then used to wash the catalyst. The combined filtrates are concentrated in vacuo to obtain an oily residue of 2-(2,2-dicyclohexylethyl)piperidine acetate.

The acetate residue is dissolved in approximately 22 liters of acetone and the temperature of the solution adjusted to about 25° C. A solution of maleic acid contained in 8 liters of warm (45° C.) acetone is rapidly added to the solution of 2-(2,2-dicyclohexylethyl) piperidine acetate solution with efficient stirring and cooled to a final temperature of 15°-20° C. The desired 2-(2,2-dicyclohexylethyl)piperidine maleate which forms is removed by filtration, washed with approximately 4 liters of cold acetone, and dried at 60°-70° C. to yield 5.5 to 5.9 kg of a product having an m.p. of 186°-9° C.

Pharmaceutical grade material is prepared by recrystallizing the maleate in approximately 46 liters of methanol, filtering to remove any insoluble material, and gradually cooling the mixture to approximately 5° C. The purified product is removed by filtration, washed with cold methanol, and dried to yield approximately 5 kg of 2-(2,2-dicyclohexylethyl)piperidine maleate having an m.p. of 189°-91° C.

EXAMPLE 5

2-(2,2-Dicyclohexylethyl)Piperidine Maleate

A solution of 100 g. (0.34 mole) of 2-(2,2-diphenylethenyl)pyridine hydrochloride contained in 400 ml. of methanol is stirred and treated with hydrogen gas at approximately 40 atmospheres in the presence of 100 g. of a 5 percent rhodium-on-carbon catalyst (Engelhard Industries) at a temperature of about 115° C. until hydrogen uptake ceases. The reaction mixture is cooled and the catalyst removed by filtration.

The filtrate is evaporated and the residue remaining is treated with a solution of 15 g. of sodium hydroxide dissolved in 50 ml. of water. The mixture is extracted with two 200 ml. portions of ethyl ether. The ether extracts are combined, dried over anhydrous magnesium sulfate, filtered and the filtrate stripped of solvent. The residue is obtained is dissolved in 500 ml. of isopropyl alcohol and treated with a hot solution of 40.7 g. of maleic acid dissolved in 170 ml. of isopropyl alcohol. The crude product which precipitates on cooling is removed by filtration. Recrystallization from methanol results in the preparation of pharmaceutically acceptable 2-(2,2-dicyclohexylethyl)piperidine maleate.

EXAMPLE 6

Effect of Catalyst Loading

Following essentially the same procedure as described in Example 4, but substituting varying amounts of catalyst, the following Table illustrates the necessity of having a catalyst loading of at least 0.15.

| (a) DPVP, kg. | (b) 5% Rh/C. q. | % Catalyst Loading | $H_2$, atm. | Temp, °C. | (c) % Product |
|---|---|---|---|---|---|
| 2.0 | 20 | .05 | 62.2 | 183 | 0 |
| 2.0 | 40 | .10 | 62.2 | 183 | 0 |
| 2.0 | 60 | .15 | 62.2 | 183 | 65.9 |
| 2.0 | 80 | .20 | 41.8 | 115 | 81.1 |
| 2.0 | 100 | .25 | 41.8 | 115 | 99.7 |
| 4.0 | 200 | .50 | 41.8 | 115 | 99.9 |

(a) 2-(2,2-diphenylethenyl)pyridine
(b) 5% rhodium-on-carbon catalyst (Engelhard Industries)
(c) Purity of crude base prior to conversion to maleate salt as determined by gas chromatography

We claim:

1. A process for the preparation of 2-(2,2-dicyclohexylethyl)piperidine which comprises reducing a glacial acetic acid solution of 2-(2,2-diphenylethenyl)pyridine with hydrogen at a pressure of 40 atmospheres and a temperature of about 115° C. in the presence of a 5 percent rhodium-on-carbon catalyst until hydrogen uptake ceases, said catalyst being present in a ratio of 0.5 parts of rhodium to 100 parts of said 2-(2,2-diphenylethenyl)pyridine, filtering said catalyst to obtain a clear filtrate, evaporating said filtrate to a residue, dissolving said residue in acetone, adding a solution of maleic acid dissolved in said solvent and recovering the precipitated 2-(2,2-dicyclohexylethyl)piperidine maleate therefrom.

* * * * *